US00PP11860P2

(12) United States Plant Patent
van Buren

(10) Patent No.: US PP11,860 P2
(45) Date of Patent: May 8, 2001

(54) ASTILBE PLANT NAMED 'VISION IN PINK'

(75) Inventor: Gert van Buren, Hillegom (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/263,855

(22) Filed: Mar. 8, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Astilbe plant named 'Vision in Pink', characterized by its upright plant habit; rapid growth rate; dark green leaves; very freely and continuous flowering; and bright pink flowers.

3 Drawing Sheets

BACKGROUND OF THE INVENTION

The present invention relates to a new and distinct cultivar of Astilbe plant, botanically known as *Astilbe chinensis*, and hereinafter referred to by the cultivar name 'Vision in Pink'.

The new cultivar is a product of a planned breeding program conducted by the Inventor in Noorden, The Netherlands. The objective of the breeding program was to develop new Astilbes with pink-colored flowers.

The new cultivar originated from a cross made by the Inventor in 1997 of the *Astilbe chinensis* cultivar 'Kremhilde', not patented, as the male or pollen parent, with the *Astilbe chinensis* cultivar 'Superba', not patented, as the female or seed parent. The cultivar 'Vision in Pink' was discovered and selected by the Inventor as a flowering plant within the progeny of the stated cross in a controlled environment in Noorden, The Netherlands.

Asexual propagation of the new cultivar by divisions at Noorden, The Netherlands, has shown the the unique features of this new Astilbe are stable and reproduced true to type in successive generations.

SUMMARY OF THE INVENTION

Plants of the cultivar 'Vision in Pink' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Visions in Pink'. These characteristics in combination distinguish 'Vision in Pink' as a new and distinct cultivar:

1. Upright plant habit.
2. Rapid growth rate.
3. Dark green leaves.
4. Very freely and continuous flowering.
5. Bright pink flowers.

Compared to plants of the purple-flowered cultivar 'Vision' (not patented), plants of the new Astilbe have pink flowers and are about 10 cm taller.

BRIEF DESCRIPTION OF THE PHOTOGRAPHS

The accompanying colored photographs illustrate the overall appearance of the new cultivar, showing the colors as true as it is reasonably possible to obtain in colored reproduction of the type. Colors in the photographs may differ slightly from the color values cited in the detailed botanical description which accurately describe the actual colors of the new Astilbe.

The photograph on the first sheet comprises a side perspective view of a typical plant of the new Astilbe grown in a landscape setting.

The photograph on the second sheet comprises a side perspective view of a typical plant of the new Astilbe grown in a container.

The photograph on the third sheet comprises a close-up view of a typical inflorescence of the new Astilbe.

DETAILED BOTANICAL DESCRIPTION

The following description, color references are made to The Royal Horticultural Society Colour Chart except where general terms of ordinary dictionary significance are used. Plants used for the description were one year-old and grown in 17-cm containers under outdoor production conditions which closely approximate commercial production conditions during the spring and summer in Noorden, The Netherlands.

Botanical classification: *Astilbe chinensis* cultivar 'Vision in Pink'.

Parentage:

*Female parent.*—*Astilbe chinensis* cultivar 'Superba', not patented.

*Male parent.*—*Astilbe chinensis* cultivar 'Kremhilde', not patented.

Propagation:

*Type.*—By root division.

*Rooting description.*—Numerous, thick and fleshy.

Plant description:

*Crop time.*—From divisions, about four to five months are required to produce fully-grown flowering plants.

*Form.*—Upright, inverted triangle, perennial herb.

*Branching habit.*—Flowering stems and leaves arise form the roots.

*Plant height.*—About 80 cm.

*Area of spread.*—About 60 cm.

*Vigor.*—Moderate; rapid growth rate.

*Stems.*—Internode length: About 12 to 15 cm. Texture: Many soft pale brown hairs, about 1 to 5 mm in length. Color: 143A.

*Foliage description.*—Arrangement: Bi-ternately compound; alternate. Quantity of leaflets per leaf: Typically about 9. Leaf length, including petiole: Up to 40 cm. Leaf width: About 20 to 30 cm. Leaflet length: About 4 to 9.5 cm. Leaflet width: About 2 to 6.5 cm. Leaflet shape: Ovate. Leaflet apex: Acute to apiculate. Leaflet base: Rounded to attenuate. Leaflet margin: Double serrate. Leaflet texture: Both surfaces with short, stiff pale green hairs, about 1 mm in length. Leaflet color: Young foliage, upper surface: 146A. Young foliage, lower surface: 146B to 147B. Mature foliage, upper surface: 137A. Mature foliage, lower surface: 137C. Venation, upper surface: 137A. Venation, lower surface: 137B to 137C. Petiole: Length: About 7 to 25 cm. Diameter: About 2 to 3 mm. Texture: Soft, pale brown hairs, about 1 to 5 mm in length. More sparsely covered than flowering stems. Color: 143B to 143C; base, 59A to 184B.

Flower description:

*Flower type and habit.*—Numerous small single flowers arranged in branched panicles. Very freely flowering with about 1,200 to 1,500 flowers and flower buds per plant. Flowers sessile.

*Natural flower season.*—Continuously flowering typically during the late summer and fall, July through October, in the Northern Hemisphere.

*Flower longevity.*—Flowers last a few weeks on the plant and more than one week as a cut flower. Flowers persistent.

*Fragrance.*—Faint, sweet.

*Flower buds.*—Length: About 2 to 3 mm. Diameter: About 2 mm. Shape: Ovate to orbicular. Rate of opening: About two to three weeks from visible bud to fully opened flower. Color: 63B to 63C.

*Flower size.*—Length: About 1.5 mm. Diameter: About 3 to 4 mm.

*Petals.*—Arrangement: Five to seven, fused. Shape: Ovate. Apex: Acute to obtuse. Margin: Entire. Length: About 2.5 to 3 mm. Width: About 1 mm. Texture: Smooth. Color: When opening, outer surface: 62A to 63B to 63C. Fully opened flower, outer surface: 63B to 64C; color becoming darker, 71A, with subsequent development.

*Calyx.*—Length: About 1 to 1.5 mm. Width: About 1 to 1.5 mm. Number of sepals: Five. Sepal shape: Ovate.

*Peduncles.*—Length: About 80 cm. Diameter: About 1.5 cm. Texture: Short, about 1 mm, brownish hairs. Color: 185B.

*Pedicel.*—Length: About 1 mm. Diameter: About 1 mm. Texture: Short, about 1 mm, brownish hairs. Color: 185B.

*Reproductive organs.*—Stamens: Stamen number: About ten. Anther attachment: Basifixed. Anther size: Less than 0.5 mm. Anther color: Creamy white. Pollen amount: Sparse. Pollen color: Creamy white. Pistils: Pistil number: Two or three. Pistil length: About 1.5 mm. Stigma shape: Club-shaped. Stigma colr: Close to 71A. Style length: About 1.5 mm. Style color: 63B to 64C. Ovary color: Pale creamy white, somewhat transparent.

*Seed.*—Seed development has not been observed.

Disease resistance: Plants of the new Astilbe have not been shown to be resistant to pathogens common to Astilbes.

It is claimed:

1. A new and distinct cultivar of Astilbe plant named 'Vision in Pink', as illustrated and described.

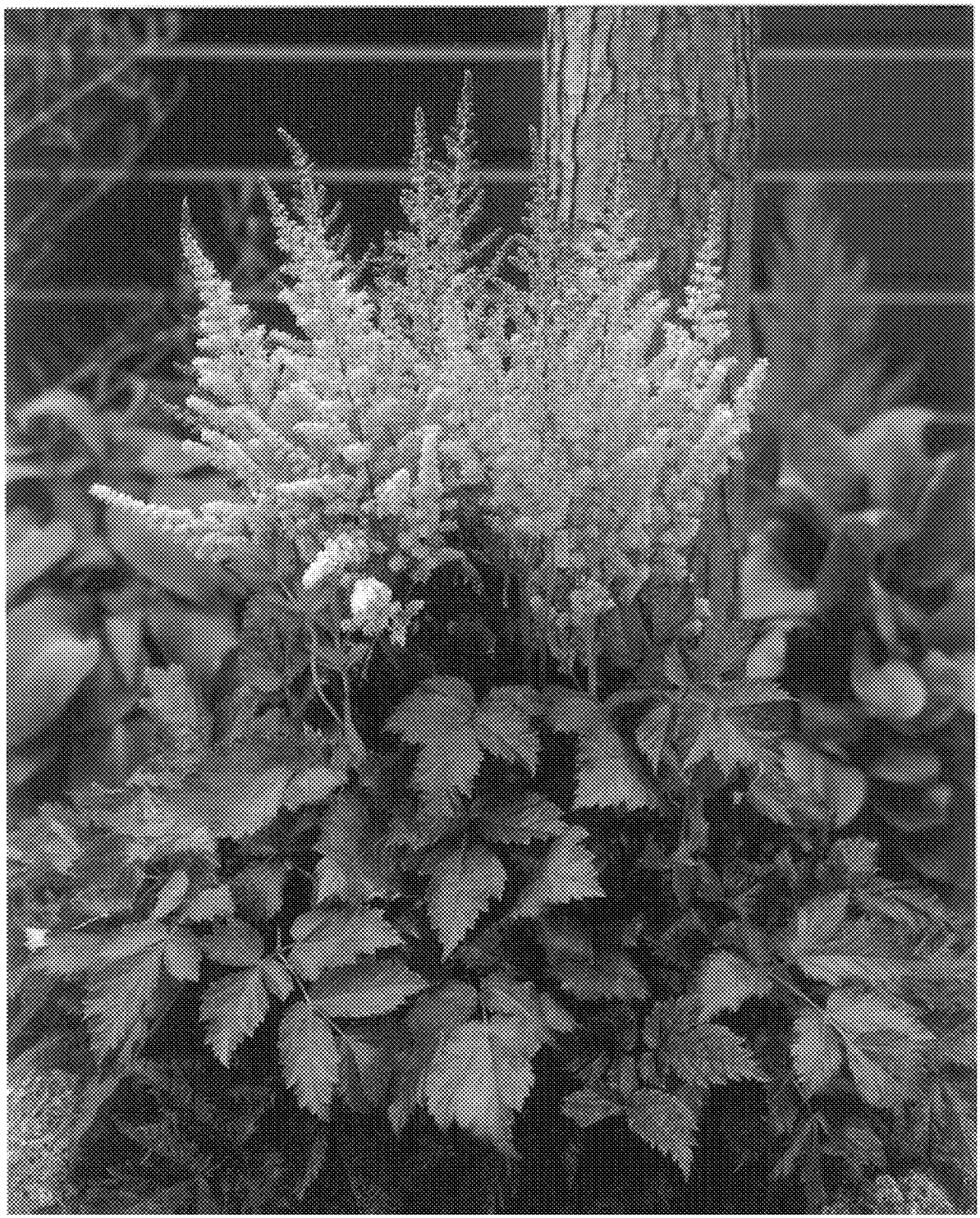

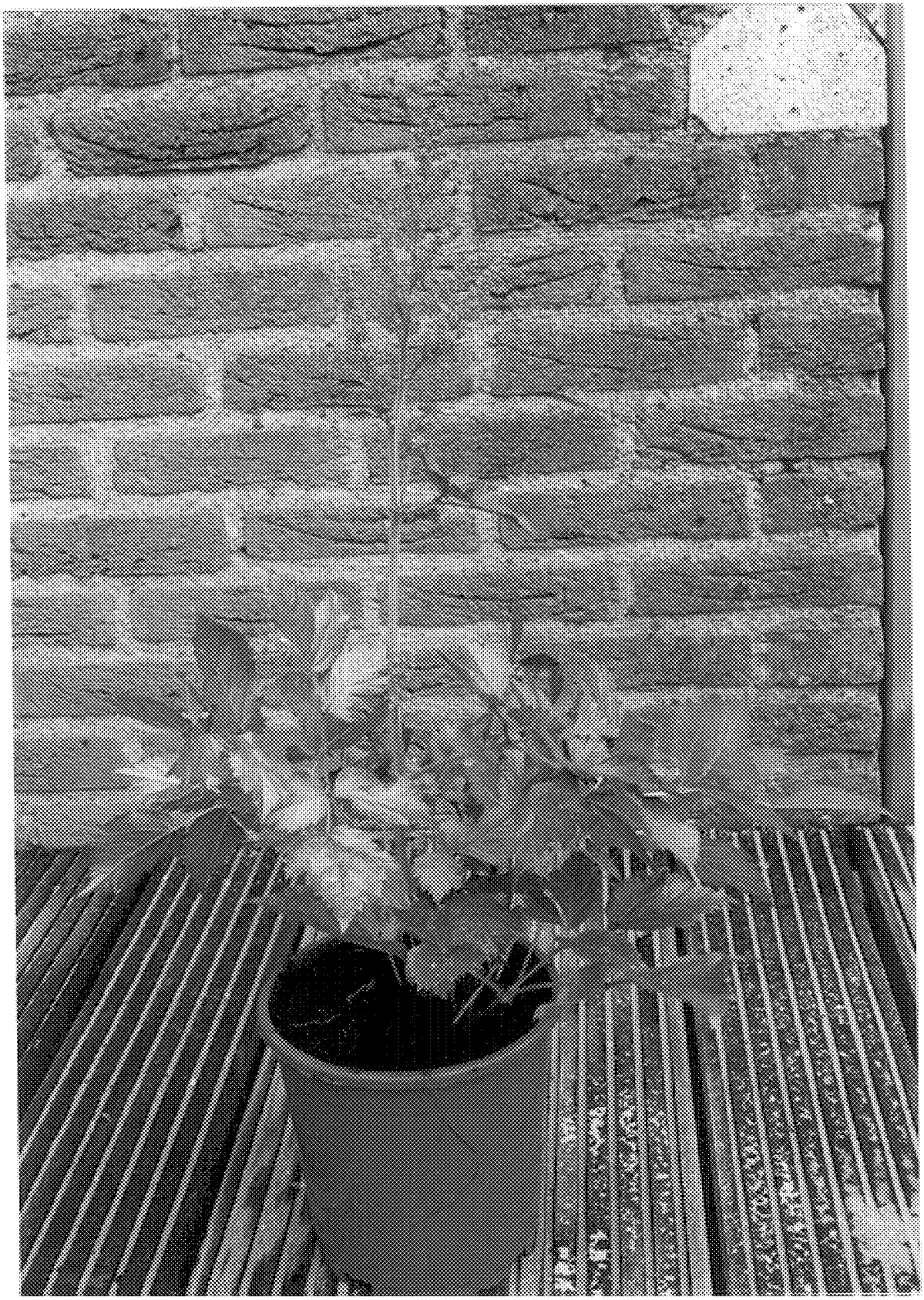

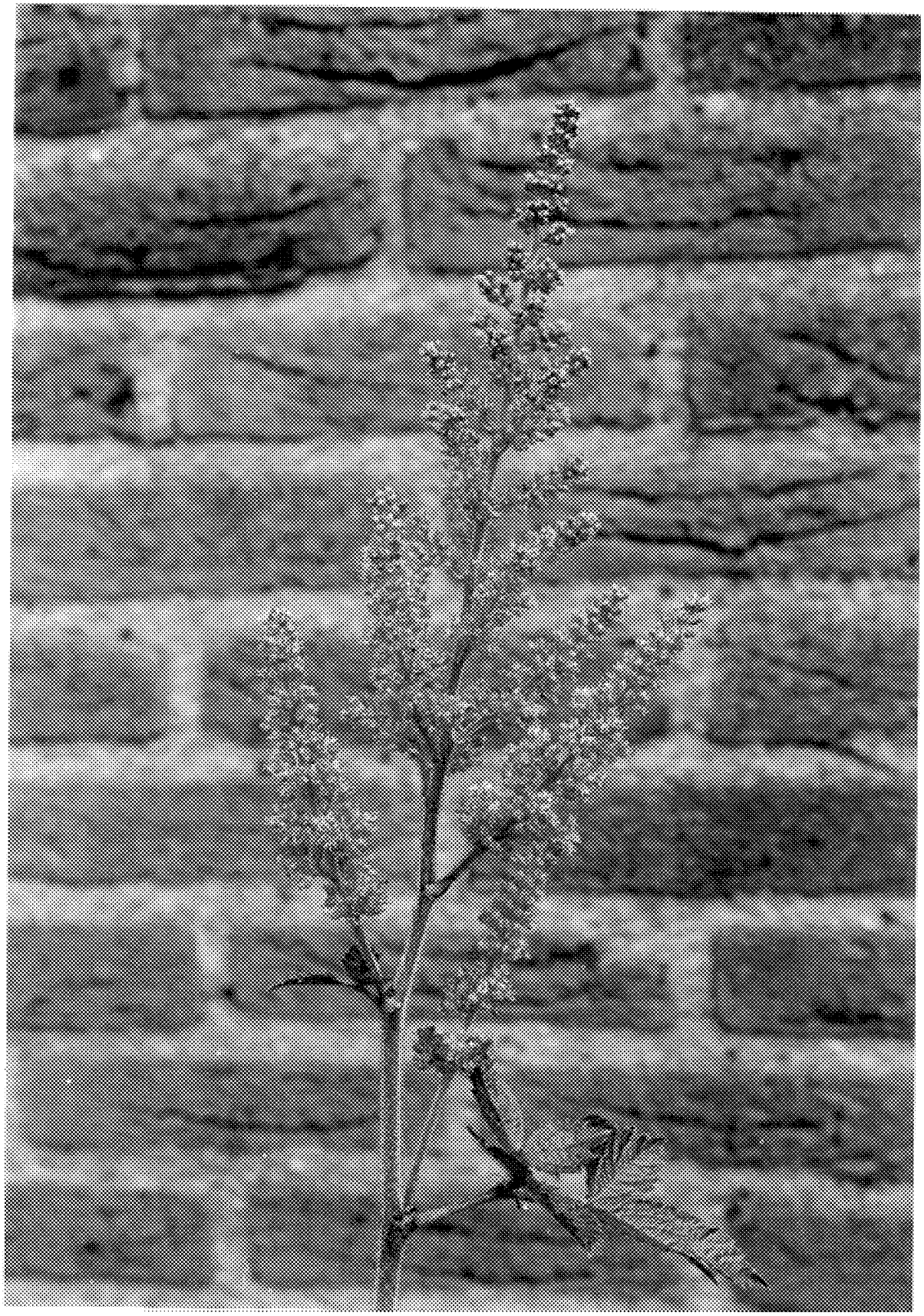

* * * * *